(12) United States Patent
Sebree et al.

(10) Patent No.: US 8,155,737 B2
(45) Date of Patent: *Apr. 10, 2012

(54) PHARMACOKINETICS OF IONTOPHORETIC SUMATRIPTAN ADMINISTRATION

(75) Inventors: Terri B. Sebree, Gladwyne, PA (US); Mark Pierce, Essex, CT (US); Carol O'Neill, Conshohocken, PA (US)

(73) Assignee: NuPathe, Inc., Conshohocken, PA (US)

( * ) Notice: Subject to any disclaimer, the term of this patent is extended or adjusted under 35 U.S.C. 154(b) by 640 days.

This patent is subject to a terminal disclaimer.

(21) Appl. No.: 12/142,604

(22) Filed: Jun. 19, 2008

(65) Prior Publication Data

US 2009/0317450 A1   Dec. 24, 2009

(51) Int. Cl.
*A61N 1/18* (2006.01)
*A61K 31/455* (2006.01)

(52) U.S. Cl. ........... 604/20; 514/299; 514/323; 424/305

(58) Field of Classification Search .................... 604/20; 424/305; 514/299, 323
See application file for complete search history.

(56) References Cited

U.S. PATENT DOCUMENTS

| | | | |
|---|---|---|---|
| 4,822,802 A | 4/1989 | Levy et al. |
| 4,927,408 A | 5/1990 | Haak et al. |
| 5,207,752 A | 5/1993 | Sorenson et al. |
| 5,358,483 A | 10/1994 | Sibalis |
| 5,458,569 A | 10/1995 | Kirk, III et al. |
| 5,466,217 A | 11/1995 | Myers et al. |
| 5,533,971 A | 7/1996 | Phipps |
| 5,605,536 A | 2/1997 | Sibalis |
| 5,651,768 A | 7/1997 | Sibalis |
| 5,685,837 A | 11/1997 | Horstmann et al. |
| 5,697,896 A | 12/1997 | McNichols et al. |
| 5,807,571 A | 9/1998 | List et al. |
| 5,941,843 A | 8/1999 | Atanasoska et al. |
| 6,035,234 A | 3/2000 | Riddle et al. |
| 6,090,095 A | 7/2000 | McNichols et al. |
| 6,171,294 B1 | 1/2001 | Southam et al. |
| 6,216,033 B1 | 4/2001 | Southam et al. |
| 6,245,347 B1 | 6/2001 | Zhang et al. |
| 6,421,561 B1 | 7/2002 | Morris |
| 6,425,892 B2 | 7/2002 | Southam et al. |
| 6,653,014 B2 | 11/2003 | Anderson et al. |
| 6,745,071 B1 | 6/2004 | Anderson et al. |
| 6,842,640 B2 | 1/2005 | Riddle et al. |
| 6,975,902 B2 | 12/2005 | Phipps et al. |
| 7,018,370 B2 | 3/2006 | Southam et al. |
| 7,302,293 B2 | 11/2007 | Southam et al. |
| 2003/0013753 A1 | 1/2003 | Aung-Din |
| 2003/0124179 A1 | 7/2003 | Jacobsen et al. |
| 2004/0242770 A1 | 12/2004 | Feldstein et al. |
| 2005/0148996 A1 | 7/2005 | Sun et al. |
| 2005/0228336 A1 | 10/2005 | Keusch et al. |
| 2006/0253061 A1 | 11/2006 | Anderson et al. |
| 2007/0093788 A1 | 4/2007 | Carter |

FOREIGN PATENT DOCUMENTS

WO  WO-2007/120747 A2  10/2007

OTHER PUBLICATIONS

Business Wire, "NuPathe reports positive phase one results for NP101 transdermal therapy for acute migraine", New York, Jun. 8, 2007, printed from ProQuest data base on Oct. 23, 2010.*

Alza Corporation (JNJ) Receives FDA Approval for IONSYS™ (Fentanyl Iontophoretic Transdermal System), retrieved online at http://www.biospace.com/news_story.aspx?NewsEntityId=19447&source=news-email (2006).

Anderson, Carter R. et al., "Effects of Iontophoresis Current Magnitude and Duration of Dexamethasone Deposition and Localized Drug Retention," *Physical Therapy*, vol. 83:161-170 (2003).

Anderson, Carter R. et al., "Quantification of Total Dexamethasone Phosphate Delivery by Iontophoresis," *International Journal of Pharmaceutical Compunding*, vol. 7(2):155-159 (2003).

Banga, Ajay K. et al., "Iontophoretic Delivery of Drugs: Fundamentals, Developments and Biomedical Applications," *Journal of Controlled Release*, vol. 7:1-24 (1988).

Chaturvedula, Ayyappa et al., "Dermal, Subdermal, and Systemic Concentrations of Granisetron by Iontophoretic Delivery," *Pharmaceutical Research*, vol. 22(8):1313-1319 (2005).

Chaturvedula, Ayyappa et al., "In vivo iontophoretic delivery and pharmacokinetics of salmon calcitonin," *International Journal of Pharmaceutics*, vol. 297:190-196 (2005).

Christensen, Michael L. et al., "Pharmacokinetics of Sumatriptan Nasal Spray in Adolescents," *J. Clin. Pharmacol.*, vol. 43:721-726 (2003).

Duquesnoy, C. et al., "Comparative clinical pharmacokinetics of single doses of sumatriptan following Subcutaneous, oral, rectal and intranasal administration," *European Journal of Pharmaceutical Sciences*, vol. 6:99-104 (1998).

Femenia-Font, A. et al., "Iontophoretic Transdermal Delivery of Sumatriptan: Effect of Current Density and Ionic Strength," *Journal of PHarmaceutical Sciences*, vol. 94(10):2183-2186 (2005).

Jadoul, Anne et al., "Transdermal Permeation of Alniditan by Iontophoresis: In Vitro Optimization and Human Pharmacokinetic Data," *Pharmaceutical Research*, vol. 13(9):1348-1353 (1996).

Jhee, Stanford S. et al., "Pharmacokinetics and Pharmacokynamics of the Triptan Antimigraine Agents," *Clin. Pharmacokinet.*, vol. 40(3):189-205 (2001).

(Continued)

*Primary Examiner* — Gina C Yu

(74) *Attorney, Agent, or Firm* — McCarter & English, LLP; Danielle L. Herritt, Esq.; A. Jacqueline Wizeman

(57) ABSTRACT

Improved pharmacokinetic profiles for the iontophoretic delivery of sumatriptan are described.

22 Claims, No Drawings

OTHER PUBLICATIONS

Kalia, Y. et al., "Transdermal iontophoretic delivery of antimigraine therapeutics in vivo," 2004 *AAPS Annual Meeting and Exposition*, (2004).

Lattin, Gary A. et al., "Electronic Control of Iontophoretic Drug Delivery," *Annals of the New Yorker Academy of Sciences*, vol. 618:450-464 (1991).

Patel, Sonal R. et al., "In vitro and in vivo evaluation of the transdermal iontophoretic delivery of sumatriptan succinate," *European Journal of Pharmaceutics and Biopharmaceutics*, vol. 66:296-301 (2007).

Patel, Sonal R. et al., "Transdermal iontophoresis of sumatriptan succinate in vitro," *205th Meeting, The Electrochemical Society, Inc.*, Abs. 725 (2004).

Patel, S.R. et al., "Transdermal iontophoretic delivery of sumatriptan in vitro," Cephalalgia, Abstracts of the 15th Migraine Trust International Symposium, (2004).

Pierce, M. et al., "NP101: A Novel Formulation of Sumatriptan Succinate Utilizing SmartRelief™ Transdermal Technology," *50th Annual Meeting American Headache Society*, p. S46, No. S17 (2008).

Scholpp, J. et al., "Early treatment of a migraine attack while pain is still mild increases the efficacy of sumatriptan," *Cephalalgia*, vol. 24:925-933 (2004).

Siegel, Steven J. et al., "A Unique Iontophoretic Patch for Optimal Transdermal Delivery of Sumatriptan," *Pharmaceutical Research*, vol. 24(10):1919-1926 (2007).

Vyteris Announces Positive Results for Phase I Clinical Trial, *Vyteris Holdings (Nevada), Inc.* (2005).

Vyteris, "The smart patch by vyteris, The future of drug delivery . . . today!" JP Morgan 25th Annual Healthcare Conference (Jan. 2007).

Xu, Xiaohui et al., "Determination of degradation products of sumatriptan succinate using LC-MS and LC-MS-MS," *Journal of Pharmaceutical and Biomedical Analysis*, vol. 26:367-377 (2001).

International Search Report and Written Opinion for No. PCT/US07/09000.

International Preliminary Examination Report for Application No. PCT/US08/81837, dated Jan. 30, 2009.

International Preliminary Examination Report for Application No. PCT/US08/81841, dated Jan. 22, 2009.

\* cited by examiner

PHARMACOKINETICS OF IONTOPHORETIC SUMATRIPTAN ADMINISTRATION

BACKGROUND

The process of iontophoresis was described by LeDuc in 1908 and has since found commercial use in the delivery of ionically charged therapeutic agent molecules such as pilocarpine, lidocaine and dexamethasone. In this delivery method, ions are carried into the skin by an electrical current that is supplied by a positive and negative electrode. Positive ions are carried away from the positive anode, while negative ions are carried away from the negative cathode.

Earlier, and some present, iontophoretic devices have been typically constructed of two electrodes attached by adhesive materials to a patient, each connected by a wire to a remote power supply. A recent publication has indicated that sumatriptan can be transdermally transported effectively using iontophoresis (Femenia-Font et al, J. Pharm Sci 94, 2183-2186, 2005). In this study, iontophoretic transport of sumatriptan was found to be at a rate 385 fold higher than passive transport.

SUMMARY

The invention pertains, at least in part to a method for treating a sumatriptan responsive state in a subject. The method includes iontophoretically administering to the subject an amount of a sumatriptan using a current of 3.5 mA or greater for at least a portion of the treatment period.

In another embodiment, the invention also pertains to a method for treating a sumatriptan responsive state in a subject. The method includes iontophoretically administering to the subject an amount of an effective amount of sumatriptan using a current of about 4 mA for a high current treatment period of about one hour and a current of about 2 mA for a subsequent low current treatment period.

In yet another embodiment, the invention pertains, at least in part, to a method for treating a sumatriptan responsive state in a subject. The method includes iontophoretically administering to a subject an amount of sumatriptan resulting in an $AUC_{0-inf}$ 95% confidence interval between about 99 hr*ng/mL and about 128 hr*ng/mL and a $C_{max}$ 95% confidence interval of between about 20 to about 28 ng/mL.

In yet another embodiment, the invention pertains, at least in part, to a method for treating a sumatriptan responsive state in a subject. The method includes administering to a subject an amount of sumatriptan resulting in a $AUC_{0-inf}$ (of sumatriptan in the subject's plasma) within a 95% confidence interval between about 99 and about 128 hr*ng/mL.

In yet another embodiment, the invention pertains, at least in part, to a method for treating a sumatriptan responsive state in a subject. The method includes administering to a subject an amount of sumatriptan resulting in a $C_{max}$ (in said subject's plasma) of between about 20 and about 28 ng/mL, or between about 23 and about 25 ng/mL and wherein the plasma concentrations of sumatriptan are sustained at therapeutic levels for at least three hours.

In yet another embodiment, the invention pertains, at least in part, to a method for treating a sumatriptan responsive state in a subject. The method includes iontophoretically administering to a subject an amount of sumatriptan resulting in an $AUC_{0-inf}$ between about 99 hr*ng/mL and about 128 hr*ng/mL and a $C_{max}$ between about 20 to about 28 ng/mL.

In yet another embodiment, the invention pertains, at least in part, to a method for treating a sumatriptan responsive state in a subject. The method includes administering to a subject an amount of sumatriptan resulting in a $AUC_{0-inf}$ (of sumatriptan in the subject's plasma) between about 99 and about 128 hr*ng/mL.

The invention also pertains, at least in part, to a method for treating a subject for a sumatriptan responsive state. The method includes administering to a subject an effective amount of sumatriptan using an iontophoretic patch for an effective treatment period. The patch may use a current density of at least about 0.10 mA/cm$^2$ or higher (e.g., about 0.30 mA/cm$^2$ or higher, or about 0.40 mA/cm$^2$) for at least a portion of the treatment period.

The invention also pertains, at least in part, to a method for treating a subject for a sumatriptan responsive state. The method includes administering to a subject an effective amount of sumatriptan using an iontophoretic patch for an effective treatment period comprising a high current density period and a low current density period. In a further embodiment, the high current density period has a current density of about 0.13 mA/cm$^2$ or higher (e.g., about 0.4 mA/cm$^2$) and said low current density period has a current density of about 0.067 mA/cm$^2$ or higher (e.g., about 0.2 mA/cm$^2$). In yet another further embodiment, the high current density period has a current density of about 0.1 mA/cm$^2$ or higher (e.g., about 0.3 mA/cm$^2$) and said low current density period has a current density of about 0.05 mA/cm$^2$ or higher (e.g., about 0.15 mA/cm$^2$).

In a further embodiment, the invention also pertains, at least in part, to a method for treating a subject for a sumatriptan responsive state. The method includes administering to the subject an effective amount of sumatriptan, wherein the effective amount of sumatriptan is administered without substantial adverse effects.

In another further embodiment, the invention also features a method of treating a sumatriptan responsive state in a subject, by transdermally administering to a subject an effective amount of sumatriptan, wherein the administration of sumatriptan results in an $AUC_{0-inf}$ coefficient of variance of less than about 25%.

In yet another further embodiment, the invention also pertains, at least in part, to a method of treating a sumatriptan responsive state in a subject. The method includes transdermally administering to the subject an effective amount of sumatriptan, wherein the administration of sumatriptan results in an $AUC_{0-inf}$ coefficient of variance less than twice the $AUC_{0-inf}$ coefficient of variance for subcutaneous administration of sumatriptan for a similar sample size.

DETAILED DESCRIPTION

One advantage of the methods of the present invention over oral administration of sumatriptan is that there is less variation of pharmacokinetic parameters with the present invention as compared to oral or nasal delivery. In contrast to oral delivery of sumatriptan, the amount of variance between the subjects after being administered sumatriptan iontophoretically is a fraction of the amount of variance between the subjects after being administered sumatriptan orally.

Another advantage the methods of the present invention is that the methods allow sumatriptan to be administered such that the $AUC_{0-inf}$ is similar to that of other dosage forms such as systemic, oral or nasal administration, while the $C_{max}$ is substantially reduced. By doing this, the amount of sumatriptan delivered systemically may be similar to the other methods, but concentration spiking is preferably reduced. Another advantage of the methods of the present invention is that the concentration of sumatriptan in the subject generally reaches therapeutic levels less than an hour after administration begins. Furthermore, therapeutic levels of sumatriptan may be maintained for a desired length of time, e.g., four to five hours.

The methods of the invention can be described, at least in part, by the use of pharmacokinetic parameters. Pharmacokinetic parameters may be calculated using methods known in the art. In the examples described herein, the pharmacokinetic parameters were calculated using a non-compartmental method, with the aid of the WinNonlin™ computer program (WinNonlin Professional, Version 5.2, Pharsight Corp, Palo Alto, Calif.). The parameters calculated include:

$AUC_{0\text{-}last}$ Area under the concentration versus time curve from time 0 to the last time point with measurable concentration ($C_t$); calculated using linear trapezoid rule.

$AUC_{0\text{-}inf}$ Area under the concentration versus time curve from time 0 to infinity; calculated as $AUC_{0\text{-}last} + C_t/\lambda_{z2}$.

$C_{max}$ Maximum observed drug concentration.

$T_{max}$ Time of maximum drug concentration.

Cl/F Apparent total body clearance; calculated as Dose/$AUC_{inf}$ and where F was assumed to be 1.0 after SQ injection $\lambda_z$ The terminal elimination phase rate constant; calculated using non-linear regression analysis $t_{1/2}$ Terminal elimination half-life; calculated as $0.693/\lambda_2$.

In one embodiment, the invention pertains, at least in part to a method for treating a sumatriptan responsive state in a subject. The method includes iontophoretically administering to the subject an amount of a sumatriptan using a current of 3.5 mA or greater for at least a portion of the treatment period.

The term "sumatriptan responsive states" includes migraines, familiar hemiplegic migraines (with and without aura), chronic paroxysmal headaches, cluster headaches, migraine headaches, basilar migraines, and atypical headaches accompanied by autonomic symptoms, such as cyclic vomiting syndrome.

The term "treat" includes the reduction or amelioration of one or more symptoms of a sumatriptan responsive state. It also may include the prevention of the occurrence or reoccurrence of the sumatriptan responsive state.

The term "effective amount" includes the amount of sumatriptan which is effective to treat a particular sumatriptan responsive state.

The term "subject" includes living organisms capable of having sumatriptan responsive states (e.g., mammals). Examples of subjects include humans, dogs, cats, horses, cows, goats, rats and mice. In one embodiment, the subject is a human. In a further embodiment, the term includes subjects suffering from a sumatriptan responsive state.

The term "iontophoretically" or "iontophoretic" includes methods of administration which use electric current to promote the absorption of a therapeutic compound (e.g., sumatriptan) from the iontophoretic device (e.g., patch) through the skin of a subject.

The term "iontophoretic patch" or "iontophoretic transdermal patch" includes devices which allow for the iontophoretic administration of sumatriptan through the skin of a subject. In one embodiment, the patch comprises electrical components, sumatriptan, and an adhesive backing layer. In a further embodiment, the iontophoretic patch may be an integrated device, e.g., a wearable, self contained devices which does not require a separate controller or power source. In another further embodiment, the iontophoretic patch of the invention is not integrated, e.g., requires a separate controller, power source, etc, and may not necessarily be wearable.

In a further embodiment, the methods of the invention use a current of about 3.6 mA or greater, about 3.7 mA or greater, about 3.8 mA or greater, about 3.9 mA or greater, about 4.0 mA or greater, about 4.1 mA or greater, about 4.2 mA or greater, or greater than about 4.5 mA to administer the sumatriptan.

Advantageously, the methods of the invention use a current of about 4.0 mA for at least a portion of the treatment period ("high current treatment period"). In a further embodiment, the high current treatment period is between about thirty minutes to about two hours, between about thirty minutes and ninety minutes, or about one hour.

In a further embodiment, the methods of the invention may also further comprise a low current treatment period (preferably, subsequent to the high current treatment period). The low current treatment period may employ a current of between about 1.5 to about 2.5 mA (e.g., about 2 mA). In another further embodiment, the low current treatment period is between about 2 hours to about 6 hours, between about 2 hours and about 5 hours, between about 2 hours and about 4 hours, or about three hours in length.

In a further embodiment, the invention also pertains, at least in part to a method for treating a sumatriptan responsive state in a subject, by iontophoretically administering to a subject an amount of sumatriptan using current of about 4 mA for a high current treatment period of about one hour and a current of about 2 mA for a subsequent low current treatment period. In a further embodiment, the sumaptriptan is iontophoretically administered using a iontophoretic patch.

In a further embodiment, the invention pertains, at least in part, to a method for treating a sumatriptan responsive state in a subject. The method includes administering to a subject an amount of sumatriptan, such that the sumatriptan responsive state is treated. In this embodiment, the amount of sumatriptan results in an $AUC_{0\text{-}inf}$ of between about 99 hr*ng/mL and about 128 hr*ng/mL (e.g., between about 107 hr*ng/mL and about 115 hr*ng/mL, or about 112 hr*ng/mL and about 114 hr*ng/mL) and a $C_{max}$ of between about 20 to about 28 ng/mL (e.g., preferably about 22.5 ng/mL and about 25 ng/mL).

In a further embodiment, the invention also pertains to a method for treating a sumatriptan responsive state in a subject. The method includes iontophoretically administering to a subject an amount of sumatriptan, resulting in an $AUC_{0\text{-}inf}$ (for sumatriptan) with a 95% confidence interval between about 99 and about 128 hr*ng/mL.

The term "confidence interval" refers, generally, to a given proportion (here 95%) which reflects the chance that a random sampling would be within these values.

In a further embodiment, the invention also pertains to another method for treating a sumatriptan responsive state in a subject. The method includes iontophoretically administering to a subject an amount of sumatriptan, resulting in an $C_{max}$ with a 95% confidence interval between about 20 and about 28 ng/mL.

In a further embodiment, the invention also pertains to yet another method for treating a sumatriptan responsive state in a subject. The method includes iontophoretically administering to a subject an amount of sumatriptan, resulting in an $C_{max}$ (in said subject's plasma for sumatriptan) of between about 20 to about 28 ng/mL, or between about 23 to about 25 ng/mL and wherein the plasma concentration of sumatriptan are sustained at therapeutic levels for at least three hours.

In a further embodiment, the term "sustained" includes levels (e.g., plasma levels of sumatriptan) which fluctuate less than about 20%, less than about 10%, or less than about 5% over a period (e.g., the low current period).

In another embodiment, therapeutic plasma level of sumatriptan occur less than one hour after the beginning of sumatriptan treatment. The term therapeutic plasma levels include levels of sumatriptan which are capable of treating a subject's symptoms for the sumatriptan response state. Examples of therapeutic levels include concentrations of between about 10-28 ng/mL of sumatriptan in the subject's plasma. In other embodiment, the therapeutic levels are between about 20-28 ng/mL.

In yet another embodiment, the invention pertains, at least in part, to a method for treating a sumatriptan responsive state in a subject. The method includes iontophoretically administering to a subject an amount of sumatriptan resulting in an $AUC_{0-inf}$ between about 99 hr*ng/mL and about 128 hr*ng/mL and a $C_{max}$ between about 20 to about 28 ng/mL.

In yet another embodiment, the invention pertains, at least in part, to a method for treating a sumatriptan responsive state in a subject. The method includes administering to a subject an amount of sumatriptan resulting in a $AUC_{0-inf}$ (of sumatriptan in the subject's plasma) between about 99 and about 128 hr*ng/mL.

In another further embodiment, the iontophoretic patch of the invention employs a current of at least about 3.5 mA (e.g., about 4 mA) for between about thirty minutes and ninety minutes (e.g., for about an hour) for a high current treatment period. The high current treatment period may further be followed by a low current treatment period. The low current treatment period may use a current of between about 1.5 mA to about 2.5 mA (e.g., about 2 mA) for between about two to about six hours (e.g., about three hours).

In another embodiment, the invention also pertains, at least in part, to a method for treating a subject for a sumatriptan responsive state. The method includes administering to the subject an effective amount of sumatriptan, wherein the effective amount of sumatriptan is administered without substantial adverse effects.

The term "substantial adverse effects" includes those listed on current triptan product labels. Examples of these substantial adverse effects include atypical sensations (e.g., sensation of warmth or cold, parethesias, etc.) and pain and pressure sensations. Examples of adverse effects include, but are not limited to, mucosal burning sensations, ear discomfort, facial pain, feeling hot, flushing, head discomfort, hot flush, paraesthesia, sense of heaviness, sensation of pressure, neck pain, etc.

In a further embodiment, the term "substantial adverse effects" do not include skin irritation or "application site disorders" caused by the patch itself.

The term "transdermal" include methods of administration of sumatriptan through the skin of a subject without substantially puncturing the skin. Examples of transdermal delivery methods include absorption, electroporation, radio frequency (RF) poration and iontophoresis.

In a further embodiment, the methods of the invention include a method of treating a sumatriptan responsive state in a subject, by transdermally administering to the subject an effective amount of sumatriptan, such that the administration of sumatriptan results in an $AUC_{0-inf}$ coefficient of variance of less than about 25%. In a further embodiment, the coefficient of variance is less than about 20% (for a group of subjects when administered the same dosage of sumatriptan using the same method and treatment profile).

The coefficient of variance can be measured is a measure of the variation of a set of data points. It is calculated by dividing the standard deviation by the mean.

In another further embodiment, the invention features a method of treating a sumatriptan responsive state in a subject, by transdermally administering to the subject an effective amount of sumatriptan, such that the sumatriptan responsive state is treated. In this method, the administration of sumatriptan results in an $AUC_{0-inf}$ coefficient of variance less than twice the $AUC_{0-inf}$ coefficient of variance for subcutaneous administration of sumatriptan for a similar sample size (e.g., the $AUC_{0-inf}$ CV for the sumatriptan administered to subjects using iontophoresis will be less than twice the $AUC_{0-inf}$ CV for a similarly sized group of subjects administered sumatriptan subcutaneously).

In an embodiment, the invention pertains, at least in part, to an iontophoretic transdermal patch for the delivery of sumatriptan or a salt thereof. The patch comprises an anode reservoir, a cathode reservoir and appropriate electrical circuitry for performing the methods of the invention.

The invention pertains, at least in part, to a method for treating a subject for a sumatriptan responsive state. The method includes administering to a subject an effective amount of sumatriptan using an iontophoretic patch for an effective treatment period. The patch may use a current density of at least about 0.10 mA/cm$^2$ or higher, 0.2 mA/cm$^2$ or higher, 0.30 mA/cm$^2$ or higher, or about 0.4 mA/cm$^2$ or higher for at least a portion of the treatment period.

In one embodiment, the effective amount is effective to treat a migraine. In this case, the effective amount of sumatriptan may be a concentration of about 10 ng/mL or greater, about 11 ng/mL or greater, about 12 ng/mL or greater, about 13 ng/mL or greater, about 14 ng/mL or greater, about 15 ng/mL or greater, about 16 ng/mL or greater, about 17 ng/mL or greater, about 18 ng/mL or greater, about 19 ng/mL or greater, about 20 ng/mL or greater, about 21 ng/mL or greater, about 22 ng/mL or greater, or about 22.5 ng/mL or greater in said subject's blood or plasma. In another embodiment, the effective amount of sumatriptan is greater than about 5 mg, greater than about 10 mg, or greater than about 15 mg. In one further embodiment, the effective amount of sumatriptan is about 10 to about 25 ng/mL in said subject's plasma.

In certain embodiments, the patch has an iontophoretically active surface area of about 10 cm$^2$ or greater, 15 cm$^2$ or greater, 17.5 cm$^2$ or greater, 20 cm$^2$ or greater, 22.5 cm$^2$ or greater, 25 cm$^2$ or greater, 27.5 cm$^2$ or greater or 30 cm$^2$ or greater.

Preferably, the high current density period precedes the low current density period. Furthermore, preferably, the current density of these periods are different and the current density of the high current density period is at least 10%, at least 30%, at least 40%, at least 50%, or at least 100% greater than the current density of the low current density period.

In a further embodiment, the treatment period comprises two portions, e.g., a high current density period and a lower current density period. Preferably, the higher current density period precedes the lower current density period. Although not to be limited by theory, it is believed that having the higher current density period first may provide relief for the subject for one or more the symptoms of the sumatriptan responsive state, e.g., migraine. The lower current density period may then prevent or delay the reoccurrence of the sumatriptan responsive state.

In one embodiment, the higher current density period is about 30 minutes to about 90 minutes, e.g., about an hour. The length and intensity of the higher current density period may be selected such that the subject may be treated for the acute symptoms of the sumatriptan responsive state. For example, the higher current density period may provide the subject with an effective dose of sumatriptan such that the primary symptoms of the sumatriptan responsive state, e.g., migraine, are eliminated or ameliorated.

In another further embodiment, when the iontophoretic pad is about 30 cm$^2$, the current density of the higher current density period is about 0.10 mA/cm$^2$ to about 0.18 mA/cm$^2$. The higher current densities allows for the quick delivery of therapeutically effective amounts of sumatriptan. Examples of currents which are used for the high current density periods include currents of about 2.5 mA to about 5 mA, e.g., about 3 mA to about 4 mA. In another further embodiment wherein the iontophoretic pad is about 10 cm$^2$, the current densities may be between about 0.25 mA/cm$^2$ to about 0.5 mA/cm$^2$, or about 0.3 mA/cm$^2$ to about 0.4 mA/cm$^2$.

In another embodiment, the lower current density period is about two hours or longer, three hours or longer, four hours or longer, or five hours or longer. The lower current density period may be selected such that the subject is effectively treated for the sumatriptan responsive state, e.g., migraine. The lower current density time may be selected such that it is effective to ameliorate the symptoms of the sumatriptan responsive state or prevent the immediate reoccurrence of the sumatriptan responsive state.

In a further embodiment, the current density of the low current density period for a 30 cm$^2$ patch is between about 0.04 mA/cm$^2$ and 0.09 mA/cm$^2$, or about 0.05 mA/cm$^2$ to about 0.08 mA/cm$^2$. Preferably, the low current density period is selected such that it treats the subject for the sumatriptan responsive state. In one embodiment, the low current density period is about 2 hours or longer, about 2.5 hours or longer, about 3 hours or longer, about 3.5 hours or longer, about 4 hours or longer, about 4.5 hours or longer, about 5 hours or longer, about 5.5 hours or longer, or about 6 hours or longer. In another further embodiment, the low current density period is about 2.5 to about 6 hours long. In a further embodiment, the current density of the low current density period for a 10 cm$^2$ patch is between about 0.125 mA/cm$^2$ and 0.25 mA/cm$^2$, or about 0.15 mA/cm$^2$ to about 0.2 mA/cm$^2$.

In another further embodiment, the low current density period uses a current of between about 1.25 mA to about 2.5 mA, or between about 1.5 mA to about 2 mA.

Preferably, the patch does not substantially irritate a subject's skin when used in accordance with the methods of the invention. The language "does not substantially irritate a subject's skin" includes patches which result in a skin erythema score of 1.50 or less, or 1.00 or less about two hours after patch removal. In another further embodiment, the language "does not substantially irritate a subject's skin" includes patches which result in a skin erythema score of 2.00 or less, or 1.00 or less immediately after patch removal.

In one embodiment, the invention also pertains to a method for treating a subject for a sumatriptan responsive state. The method includes administering to the subject an effective amount of sumatriptan using an iontophoretic patch for an effective treatment period comprising a high current density period and a low current density period.

In another embodiment, the high current density period has a current density of between about 0.1 mA/cm$^2$ and about 0.3 mA/cm$^2$ and the low current density period has a current density of between about 0.05 mA/cm$^2$ and about 0.15 mA/cm$^2$. In this embodiment, the high current density period may be about 1 hour and the low current density period may be about five hours.

In yet another embodiment, the high current density period has a current density of between about 0.13 mA/cm$^2$ and about 0.4 mA/cm$^2$ and the low current density period has a current density of between about 0.067 mA/cm$^2$ and about 0.2 mA/cm$^2$. In this embodiment, the high current density period may be about 1 hour and the low current density period may be about three to five hours.

EXEMPLIFICATION OF THE INVENTION

Example 1

Use of Iontophoretic Patches to Deliver Sumatriptan Succinate

A single center, open label, single-dose, five period study was conducted to compare the pharmacokinetics of four prototypes of sumatriptan iontophoretic transdermal patches of the invention with 100 mg oral sumatriptan succinate in healthy volunteers. Subjects, at minimum, participated in Treatment A and Treatment B.

The iontophoretic patches used were self-contained, with an external power source, designed to be applied to the surface of the skin and to deliver medication systemically.

The patch treatments and prototype iontophoretic patches prepared for this example, are detailed in the Table 1 below.

TABLE 1

Iontophoretic Patch Dosing Treatments

| Period | Treatment | Placement | Wear Time(hr) | Waveform | Theoretical Delivery Dose | mA Minutes | Anode Electrode Size |
|---|---|---|---|---|---|---|---|
| 1 | A | Upper arm | 6 | 3 mA for 1.0 hr then 1.5 mA for 5.0 hrs | 3 mg/hr × 1 hr + 1.5 mg/hr × 5 hrs = 10.5 mg | 630 | 5 cm$^2$ |
| 3 | C | Upper arm | 6 | 3 mA for 1.0 hr then 1.5 mA for 5.0 hrs | 3 mg/hr × 1 hr + 1.5 mg/hr × 5 hrs = 10.5 mg | 630 | 5 cm$^2$ |
| 4 | D | Upper back | 6 | 4 mA for 1.0 hr then 2.0 mA for 5.0 hrs | 4 mg/hr × 1 hr + 2 mg/hr × 5 hr = 14.0 mg | 840 | 10 cm$^2$ |
| 5 | E | Upper back | 4 | 4 mA for 1.0 hr then 2.0 mA for 3.0 hrs | 4 mg/hr × 1 hr + 2 mg/hr × 3 hr = 10.0 mg | 600 | 10 cm$^2$ |

Nine subjects participated in Treatment B a 100 mg sumatriptan succinate oral tablet. The study consisted of a Screening Visit followed by Treatments A, B, C, D and E. Each of the treatment periods were separated by a 2 day washout period. During the screening period, each subject had a physical examination, including vital signs, a hepatitis screen, HIV screen, urine drug screening, an electrocardiogram, pregnancy test (females only), ethanol breath test and clinical laboratory tests. In addition, the medical history and demographic data including age and race was recorded. All assessments were conducted no more than 28 days prior to the first dosing. Subjects who met all of the inclusion criteria and none of the exclusion criteria were admitted on Day-1. During the confinement periods, subjects did not engage in strenuous activity and abstained from alcohol and tobacco. During each confinement period, the subjects received study dosing after an overnight fast. The subjects were dosed at 0800 hours on Day 1 of each dosing period. For periods 1 and 2, the subjects were confined to the study center the morning before dosing of Treatment A (Day-1) and through the 24 hour post dose assessments for Treatment B.

For periods 3-5, the subjects were confined to the study center the morning before dosing of Treatment C (Day-1) and through the 24 hour post dose assessments for Treatment E. Each dosing period lasted approximately 2 days with at least a 2 day washout period between dosings. Study participants were between 19 and 50 years old.

The patches for Treatments A and C were applied to a clean, dry, relatively hair free area of the upper arm. Treatments were applied to alternating arms. The NP101 patches for Treatments D and E were applied to a clean, dry, relatively hair free area of the upper back. Treatments were applied to alternating right and left positions on the upper back. PK blood samples were scheduled for collection per subject for each of the five periods.

For Treatments A and B, 4 mL blood samples for sumatriptan plasma concentrations were collected by catheter or venipuncture into EDTA collection tubes at the scheduled collection times. For Treatments C, D and E, 2.7 mL blood samples for sumatriptan plasma concentrations were collected by catheter or venipuncture into EDTA collection tubes at the scheduled collection times. Blood samples were cooled in an ice bath and centrifuged as soon as possible after collection. Plasma samples were stored in labeled tubes at −20° C. Standard safety assessments were also performed during each treatment period and at the conclusion of the study, including adverse event monitoring, clinical safety laboratory tests, and vital signs. Iontophoretic delivery system assessments including adhesion and dermal irritation and the amount of adhesive residue on the skin were performed during Treatments A, C, D and E.

The subjects were healthy adult volunteers (four males and five females) who were willing to attend the clinic for five treatment periods. The subjects received no other medication (prescription or over-the-counter) for two weeks prior to study entry, unless approved by the designated physician. Study participants were between 19 and 50 years old. The mean age was 28 years old.

The five treatments, as described in Table 1, were administered in five clinical periods. Four of the five dosing treatments were using the patches comprising the formulations of the invention. The patch was applied to the upper arm or upper back depending on the Treatment period.

In treatment B, the subjects received an Imigran FTab oral tablet (100 mg sumatriptan succinate) with 240 mL of water after an overnight fast. Subjects remained fasted for 4 hours after dosing.

The drug reservoir pad (anode) formulation for Treatment A, C, D and E was: 10% polyamine formulation plus 4% sumatriptan succinate (loaded with up to 120 mg of sumatriptan).

The salt reservoir pad (cathode) formulation for Treatments A, C, D and E was: 2% hydroxypropylcellulose (HPC) and NaCl.

There were no serious adverse events reported during the study periods. The most frequently reported adverse event was headache related to Treatment B (sumatriptan succinate 100 mg oral tablet) and tingling and itching at patch site for patch treatments A, C, D and E.

Mean skin erythema scores were also calculated for each of the patch treatments. Immediately after patch removal, mean scores were 1.40 or below for each of the four patch treatments. After 72 hours, the mean scores were each below 1.00.

Nine subjects were dosed with patch Treatment A and Treatment B, the 100 mg sumatriptan oral tablet. Seven subjects were treated with patch Treatments C, D, and E. Descriptive statistics for the PK parameters, $AUC_{0-inf}$, $AUC_{0-last}$, $C_{max}$, $T_{max}$, Lambda and $t_{1/2}$, were calculated. Arithmetic means of $AUC_{0-inf}$ range from 99 to 144 ng/mL for patches (Treatment A: 99 ng/mL; Treatment C: 99 ng/mL; Treatment D: 144 ng/mL; and Treatment E: 105 ng/mL) and is about 225 ng/mL*h for Treatment B. Arithmetic means of half-life (T1;2) range from 2.6 to 3 hours for the patches (Treatment A: 3.0 hr; Treatment C: 2.7 hr; Treatment D: 2.6 hr; and Treatment E: 2.5 hr) and is about 3.4 hours for Treatment B.

The results of analysis of variance among the treatment groups in $AUC_{0-inf}$, $AUC_{0-last}$ and $C_{max}$ were also analyzed. Treatment B (sumatriptan 100 mg oral tablet) is statistically different ($p<0.001$) from all patch treatments (A, C, D, and E) studied in all PK parameters. Treatment A and C are somewhat similar in their PK profile; both are different from Treatment D in $AUC_{0-inf}$, $AUC_{0-last}$, and $C_{max}$; both are not different from Treatment E in AUCs. Furthermore, both Treatment A and Treatment C have lower $C_{max}$ compared to Treatment E.

Example 2

Study of Patch Pharmacokinetics as Compared to Oral, Nasal and Subcutaneous Injections of Sumatriptan In this example, the iontophoretic patches of the invention were compared to the currently approved oral, subcutaneous (SQ) injection and nasal spray formulations of Imitrex® in healthy volunteers. The bioavailability of the drug was compared to the bioavailability relative to the 6 mg SQ injection.

This was a single center, open label, randomized, single-dose, crossover study, wherein subjects were to receive seven study treatments in sequence according to the randomization schedule, separated by a 3 to 10 day washout period.

The drug being tested was sumatriptan succinate in the iontophoretic patch of the invention. The patch was compared to three formulations of Imitrex® (100 mg oral sumatriptan succinate tablet (Treatment B), 6 mg subcutaneous injection (Treatment C) and 20 mg intranasal spray (Treatment D)).

Subjects were admitted on Day-1, at least 12 hours prior to dosing on Day 1 of each treatment period, and remained in the clinical unit under supervision until the last PK sample was obtained. During each treatment period, blood was obtained at prescribed times for PK analysis.

Subjects

A total of 25 subjects (12 females and 13 males) were enrolled in the study and all received sumatriptan. Overall, 16 (64%) subjects completed the study. As indicated in Table 2 four subjects withdrew consent; 3 subjects discontinued the study due to an adverse event; 1 subject was lost to follow-up; and, 1 subject discontinued due to a protocol violation. Study participants were between 21 and 57 years old.

All 25 enrolled subjects were treated with sumatriptan: 23 subjects received control treatments (Treatments B (100 mg oral sumatriptan succinate tablet), C (6 mg subcutaneous injection), and D (20 mg intranasal spray)) and 17 subjects had at least one patch of the invention (Treatments A, E, F or G, as shown in Table 2).

TABLE 2

| Treatment | Worn | Wear Time (hr) | Waveform | mA Min | Anode Reservoir | Cathode Reservoir |
|---|---|---|---|---|---|---|
| A, F | Upper arm | 4 | 4 mA 1.0 hr then 2.0 mA for 3.0 hrs | 600 | 3.0 g of sumatriptan gel solution (10% polyamine and 4% sumatriptan succinate) containing 120 mg of sumatriptan succinate | 3.0 g of 2% Hydroxypropyl cellulose (HPC) and NaCl |
| E, G | Upper arm | 4 | 4 mA 1.0 hr then 2.0 mA for 3.0 hrs | 600 | 2.6 g of sumatriptan gel solution (10% polyamine and 4% sumatriptan succinate) containing 104 mg of sumatriptan succinate | 2.6 g of 2% Hydroxypropyl cellulose (HPC) and NaCl |

Phamacokinetic Analysis

Serial blood samples for PK analysis were collected by catheter or venipuncture into EDTA collection tubes at predetermined times according to treatment for the determination of sumatriptan concentrations in plasma. The plasma samples were analyzed by a validated HPLC with MS/MS detection.

The following PK parameters were determined: $C_{max}$, $T_{max}$, $\lambda_z$, $t_{1/2}$, $AUC_{0-last}$, $AUC_{0-inf}$ and total body clearance (Cl/F). The bioavailability (F) of the non-parenteral formulations were assessed relative to the SQ injection.

PK parameters for sumatriptan were calculated from the actual plasma concentration-time data using non-compartmental method with WinNonlin™ computer program. PK parameters for each treatment were reported along with descriptive statistics.

Analysis of variance (ANOVA) was used to compare $AUC_{0-inf}$ and $C_{max}$ values between treatments. $AUC_{0-last}$, $T_{max}$ and $t_{1/2}$ were summarized descriptively.

The mean clearance for the 17 subjects who had Treatments F and G was 54483 mL/hr. Table 3 below provides a summary of arithmetic means of the pharmacokinetic parameters for each treatment group.

TABLE 3

| Treatment Group[1] | $AUC_{0-inf}$ (hr * ng/mL) | $AUC_{0-last}$ (hr * ng/mL) | $C_{max}$ (ng/mL) | $T_{max}$ (hr) | $t_{1/2}$[2] (hr) | Lambda_z (/hr) |
|---|---|---|---|---|---|---|
| SQ (n = 23) | 113.60 | 111.42 | 82.24 | 0.25 | 2.21 | 0.31 |
| Nasal (n = 23) | 50.25 | 48.72 | 12.49 | 1.45 | 2.24 | 0.31 |
| Oral (n = 23) | 247.14 | 237.40 | 51.61 | 2.24 | 4.82 | 0.16 |
| Treatment F (n = 17) | 113.45 | 111.51 | 24.76 | 1.65 | 2.94 | 0.22 |
| Treatment G (n = 17) | 112.92 | 111.01 | 23.05 | 2.53 | 2.86 | 0.23 |

[1] Treatment groups: B = Oral, C = SQ, D = Nasal, F = Patch Treatment F, and G = Patch Treatment G
[2] $t_{1/2} = 0.693/\text{Lambda\_z}$ Pharmacokinetic parameters, including $AUC_{0-inf}$, $AUC_{0-last}$, $C_{max}$, Lambda_z, $t_{1/2}$, and $T_{max}$, for the two patches of the invention and the three positive controls (Treatments B, C, and D) are outlined in Table 4 (Arithmetic Means). The parameters derived directly from the plasma concentration data are presented as "observed parameters"; AUC and $C_{max}$ derived directly from the plasma concentration data.

TABLE 4

Pharmacokinetic Parameters by Treatment Group

| Parameter | Group[1] | n | Arithmetic Mean (95% CI) | | | Min | Max | Median | CV (%) | SD |
|---|---|---|---|---|---|---|---|---|---|---|
| | | | Mean | Lower | Upper | | | | | |
| $AUC_{0-inf}$ (hr * ng/mL) | SQ | 23 | 113.60 | 106.57 | 120.64 | 79.40 | 135.44 | 113.81 | 14.3 | 16.261 |
| | Nasal | 23 | 50.25 | 40.80 | 59.71 | 5.27 | 99.21 | 51.03 | 43.5 | 21.873 |
| | Oral | 23 | 247.14 | 215.19 | 279.09 | 155.66 | 457.51 | 230.44 | 29.9 | 73.890 |
| | Patch F | 17 | 113.45 | 99.04 | 127.86 | 67.10 | 157.57 | 106.83 | 24.7 | 28.028 |
| | Patch G | 17 | 112.92 | 102.49 | 123.34 | 76.70 | 146.58 | 117.13 | 18.0 | 20.276 |
| $AUC_{0-last}$ (hr * ng/mL) | SQ | 23 | 111.42 | 104.37 | 118.46 | 77.71 | 134.57 | 112.19 | 14.6 | 16.292 |
| | Nasal | 23 | 48.72 | 39.35 | 58.08 | 4.67 | 97.97 | 49.96 | 44.4 | 21.652 |
| | Oral | 23 | 237.40 | 205.71 | 269.08 | 148.74 | 451.62 | 221.61 | 30.9 | 73.265 |
| | Patch F | 17 | 111.51 | 97.29 | 125.74 | 65.79 | 155.76 | 105.50 | 24.8 | 27.665 |
| | Patch G | 17 | 111.01 | 100.70 | 121.31 | 74.77 | 143.39 | 115.73 | 18.1 | 20.045 |

TABLE 4-continued

Pharmacokinetic Parameters by Treatment Group

| Parameter | Group[1] | n | Arithmetic Mean (95% CI) | | | Min | Max | Median | CV (%) | SD |
|---|---|---|---|---|---|---|---|---|---|---|
| | | | Mean | Lower | Upper | | | | | |
| $C_{max}$ (ng/mL) | SQ | 23 | 82.24 | 75.59 | 88.89 | 52.10 | 108.0 | 83.10 | 18.7 | 15.369 |
| | Nasal | 23 | 12.49 | 10.12 | 14.85 | 2.25 | 26.10 | 11.30 | 43.8 | 5.468 |
| | Oral | 23 | 51.61 | 43.15 | 60.07 | 22.40 | 108.0 | 47.50 | 37.9 | 19.567 |
| | Patch F | 17 | 24.76 | 21.4 | 28.115 | 13.6 | 38 | 24.1 | 26.368 | 6.528 |
| | Patch G | 17 | 23.05 | 20.49 | 25.609 | 14.3 | 33.3 | 23.8 | 21.618 | 4.982 |
| $T_{max}$ (hr.) | SQ | 23 | 0.25 | 0.21 | 0.28 | 0.17 | 0.33 | 0.17 | 33.1 | 0.082 |
| | Nasal | 23 | 1.45 | 1.08 | 1.82 | 0.17 | 4.00 | 1.50 | 58.3 | 0.846 |
| | Oral | 23 | 2.24 | 1.79 | 2.69 | 0.50 | 4.00 | 2.00 | 46.1 | 1.032 |
| | Patch F | 17 | 1.65 | 1.02 | 2.28 | 1.00 | 4.00 | 1.00 | 74.2 | 1.222 |
| | Patch G | 17 | 2.53 | 1.80 | 3.26 | 1.00 | 4.00 | 3.00 | 56.1 | 1.419 |
| $t_{1/2}$[4] (hr.) | SQ | 23 | 2.21 | 1.94 | 2.47 | 1.35 | 4.12 | 2.09 | 27.7 | 0.611 |
| | Nasal | 23 | 2.24 | 1.89 | 2.60 | 1.30 | 4.79 | 2.04 | 36.7 | 0.823 |
| | Oral | 23 | 4.82 | 3.41 | 6.23 | 2.58 | 17.57 | 3.74 | 67.6 | 3.259 |
| | Patch F | 17 | 2.94 | 2.70 | 3.19 | 1.70 | 3.59 | 2.91 | 16.2 | 0.475 |
| | Patch G | 17 | 2.86 | 2.60 | 3.11 | 1.96 | 3.79 | 2.84 | 17.5 | 0.499 |
| Lambda_z (/hr.) | SQ | 23 | 0.31 | 0.28 | 0.34 | 0.16 | 0.47 | 0.31 | 24.2 | 0.075 |
| | Nasal | 23 | 0.31 | 0.28 | 0.35 | 0.13 | 0.49 | 0.31 | 27.9 | 0.087 |
| | Oral | 23 | 0.16 | 0.14 | 0.18 | 0.04 | 0.25 | 0.17 | 31.7 | 0.051 |
| | Patch F | 17 | 0.22 | 0.20 | 0.25 | 0.18 | 0.38 | 0.22 | 20.6 | 0.046 |
| | Patch G | 17 | 0.23 | 0.21 | 0.25 | 0.17 | 0.33 | 0.22 | 18.5 | 0.043 |

$AUC_{0\text{-}inf}$ arithmetic means for the 6 mg SQ injection, 100 mg oral preparation, and 20 mg nasal preparation were 114 hr*ng/mL, 247 hr*ng/mL, and 50 hr*ng/mL, respectively. Both treatments F and G yielded $AUC_{0\text{-}inf}$ of approximately 113 hr*ng/mL.

Arithmetic means of $C_{max}$ for oral, nasal, and injection groups were 51.6 ng/mL, 12.5 ng/mL, and 82.2 ng/mL, respectively. Arithmetic means of $C_{max}$ for the patches ranged from 24.7 ng/mL (Treatment F) to 23.1 ng/mL (Treatment G). $T_{max}$ was 0.25 hour for the injection, 1.45 hour for nasal, and 2.24 hour for the oral formulation. Apparent $T_{max}$ for Treatment F was 1.65 hour and Treatment G was 2.53 hour.

The elimination half-life was 2.21 hours for injection, 2.24 hours for nasal, and 4.84 hours for oral. The elimination half-life after removing the patch was 2.94 hours for Treatment F and 2.86 hours for Treatment G. The terminal half-life for the oral formulation in this study may have appeared greater than previously reported[10,11] because of the high sensitivity of PPD LCMS method used (limit of quantification equal 0.200 ng/mL), resulting in quantification of clinically insignificant levels, possibly reflecting the presence of a deep compartment.

Safety Evaluation:

There were no deaths or serious adverse events reported in this study.

There were no unexpected adverse events or a significant increase in the frequency of commonly reported adverse events in subjects receiving the patch of the invention compared with oral, nasal and subcutaneous administration of sumatriptan.

Atypical sensations, and pain and pressure sensations, which are commonly reported for oral and subcutaneous sumatriptan (as shown in Table 5), were not reported following the patch Treatments F and G patch. This may reflect in part the lower $C_{max}$ levels obtained with the patch treatments.

Adverse events were also categorized into two special groupings; (1) Atypical Sensations and (2) Pain and Pressure Sensations. This was done to be consistent with current triptan labeling which sought to capture both various short-lived side effects associated with triptans (i.e. sensation of warmth / cold, paresthesias) and which are grouped as 'Atypical Sensations', and "Pain and Pressure Sensations". The majority of these adverse events, Atypical Sensations and Pain and Pressure Sensations (Table 5), occurred in close proximity to the $T_{max}$ in subjects treated with oral and subcutaneous sumatriptan.

TABLE 5

Atypical Sensations/Pain and Pressure Sensations

| | | n (%) Subjects Reported Event | | | | |
|---|---|---|---|---|---|---|
| | Adverse Event | Treatment C SubQ | Treatment B Oral | Treatment D Nasal | Treatment F Patch F | Treatment G Patch G |
| Grouping | Preferred Term | (N = 23) | (N = 23) | (N = 23) | (N = 17) | (N = 17) |
| Atypical Sensation | Any AEs | 14 (60.9%) | 2 (8.7%) | — | — | — |
| | Burning sensation mucosal | 3 (13.0%) | — | — | — | — |
| | Ear discomfort | 1 (4.3%) | — | — | — | — |
| | Facial pain | 1 (4.3%) | — | — | — | — |
| | Feeling hot | 2 (8.7%) | — | — | — | — |
| | Flushing | 6 (26.1%) | — | — | — | — |
| | Head discomfort | 1 (4.3%) | 1 (4.3%) | — | — | — |

TABLE 5-continued

Atypical Sensations/Pain and Pressure Sensations

| | | n (%) Subjects Reported Event | | | | |
|---|---|---|---|---|---|---|
| | Adverse Event | Treatment C SubQ | Treatment B Oral | Treatment D Nasal | Treatment F Patch F | Treatment G Patch G |
| Grouping | Preferred Term | (N = 23) | (N = 23) | (N = 23) | (N = 17) | (N = 17) |
| | Hot flush | 3 (13.0%) | 1 (4.3%) | — | — | — |
| | Paraesthesia | | | — | — | — |
| | Sensation of heaviness | 1 (4.3%) | | — | — | — |
| | Sensation of pressure | 1 (4.3%) | | — | — | — |
| Pain and Pressure Sensation | Any AEs | 2 (8.7%) | 4 (17.4%) | — | — | — |
| | Neck pain | | 2 (8.7%) | — | — | — |
| | Sensation of heaviness | 1 (4.3%) | 1 (4.3%) | — | — | — |
| | Sensation of pressure | 1 (4.3%) | 1 (4.3%) | — | — | — |

Adverse events associated with the patch of the invention were in general mild and most resolved without treatment.

Regarding treatments with the iontophoretic patch of the invention overall, no subject in this study had a skin irritation score of 3 or 4 at any time. There were no subject discontinuations directly attributable to patch treatments (application site disorders). Skin irritation scores were either scored 0 or 1 by 72 hours. Skin irritation scores were statistically better (i.e., lower mean score) for Treatment F compared to Treatment G at 48 and 72 hours post patch removal. At 72 hours or at 10 day follow-up, all skin irritation scores were "0" (no erythema).

At the time of patch removal, more than 75% of the subjects had minimal or no erythema. By 48 hours post patch removal all subjects had minimal or no erythema (NB: one assessment was not done for Treatment F). At 72 hours all of the subjects treated with Treatment F had no erythema (NB: one assessment was not done for Treatment F). For subjects that had minimal erythema at 72 hours (35.3% of Treatment G subjects) the erythema completely resolved by the day 10 follow-up. In general, these findings (Table 6) were not clinically different from those observed in subjects treated with Patches A and E.

TABLE 6

Skin Irritation Mean Score - Directly Under the Drug Pad
Subjects Treated with Patches F and G

| Area | Time Point | Statistics | Patch F | Patch G |
|---|---|---|---|---|
| Skin Directly Under the Drug Pad | Patch Removal | Sample Size | 17 | 17 |
| | | Mean | 1.1 | 1.1 |
| | | Standard Deviations | 0.49 | 0.66 |
| | | Minimum | 0.0 | 0.0 |
| | | Maximum | 2.0 | 2.0 |
| | | Median | 1.0 | 1.0 |
| | 24 hours | Sample Size | 17 | 17 |
| | | Mean | 0.9 | 0.7 |
| | | Standard Deviations | 0.66 | 0.69 |
| | | Minimum | 0.0 | 0.0 |
| | | Maximum | 2.0 | 2.0 |
| | | Median | 1.0 | 1.0 |
| | 48 hours | Sample Size | 16 | 17 |
| | | Mean | 0.2 | 0.6 |
| | | Standard Deviations | 0.40 | 0.51 |
| | | Minimum | 0.0 | 0.0 |
| | | Maximum | 1.0 | 1.0 |
| | | Median | 0.0 | 1.0 |
| | 72 hours | Sample Size | 16 | 17 |
| | | Mean | 0.0 | 0.4 |
| | | Standard Deviations | 0.00 | 0.49 |
| | | Minimum | 0.0 | 0.0 |
| | | Maximum | 0.0 | 1.0 |
| | | Median | 0.0 | 0.0 |

Overall, the safety profile seen in this study reflects the known safety profile of oral, subcutaneous and nasally administered sumatriptan. Sumatriptan administration via the patch did not reveal any unexpected adverse events and was well tolerated.

Results

The pharmacokinetic results for Treatments B, C, and D (the subcutaneous, oral and nasal methods of administering) were comparable to those presented in the approved product labels. The sumatriptan plasma concentration time curves for both the iontophoretic patches of the invention were not substantially different from each other, 10 indicating that transdermal delivery of sumatriptan is not significantly influenced by differences in formulation loading in the 2.6-3.0 gram range. Treatments using the patches of the invention yielded pharmacokinetics of plasma sumatriptan intermediate between Treatment D (20 mg sumatriptan nasal spray) and Treatment B (100 mg sumatriptan oral tablets). The patches of the invention delivered sumatriptan with $C_{max}$ of 23-25 ng/mL and sustained plasma concentrations of sumatriptan in this range for the full 4 hours of current flow. These results confirm and extend pharmacokinetic data obtained in Example 1.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for treating a sumatriptan responsive state in a human, comprising iontophoretically administering to said human an effective amount of sumatriptan using a current of about 4 mA for a high current treatment period of about one hour and a current of about 2 mA for a subsequent low current treatment period, such that said human is treated for said sumatriptan responsive state,
   wherein the sumatriptan is administered such that an $AUC_{0-inf}$ of between about 67 and about 158 hr*ng/mL within a 95% confidence interval is achieved in the human's plasma; and
   wherein the sumatriptan is administered such that a $C_{max}$ of between about 14 and about 38 ng/mL within a 95% confidence interval is achieved in the human's plasma.

2. The method of claim 1, wherein said amount of sumatriptan is about 10 mg.

3. The method according to claim 1, wherein the sumatriptan is administered such that an $AUC_{0-inf}$ between about 99 and 128 hr*ng/mL within a 95% confidence interval is achieved in the human's plasma and a $C_{max}$ between about 20 and about 28 ng/mL within a 95% confidence interval is achieved in the human's plasma.

4. The method of claim 3, wherein about 10 mg of sumatriptan is administered to said human.

5. The method according to claim 1, wherein the sumatriptan is administered such that an $AUC_{0-inf}$ between about 99 and about 128 hr*ng/mL within a 95% confidence interval is achieved in the human's plasma; or
   wherein the sumatriptan is administered such that a $C_{max}$ between about 20 and about 28 ng/mL within a 95% confidence interval is achieved in the human's plasma; or
   wherein the sumatriptan is administered such that a $C_{max}$ of about 23-25 ng/mL is achieved and plasma concentrations are sustained for at least three hours; or
   wherein the sumatriptan is administered such that an $AUC_{0-inf}$ between about 99 and 128 hr*ng/mL and a $C_{max}$ between about 20 to about 28 ng/mL are achieved in the human's plasma.

6. The method according to claim 1, wherein said effective amount of sumatriptan is administered without substantial adverse effects.

7. The method of claim 6, wherein said adverse effects comprise pain, pressure sensations or atypical sensations.

8. The method according to claim 1, wherein said administration of sumatriptan results in an $AUC_{0-inf}$, $t_{1/2}$, or $C_{max}$ coefficient of variance (CV) of less than about 25%.

9. The method according to claim 1, wherein said administration of sumatriptan results in an $AUC_{0-inf}$ coefficient of variance less than twice the $AUC_{0-inf}$ coefficient of variance for subcutaneous administration of sumatriptan.

10. The method of claim 1, wherein said effective amount of sumatriptan is administered without substantially irritating said human's skin.

11. The method of claim 10, wherein said iontophoretic administration of sumatriptan causes little or no erythema.

12. The method of claim 10, wherein said iontophoretic administration of sumatriptan causes little or no punctuate lesions.

13. The method of claim 1, wherein said sumatriptan responsive state is a migraine.

14. A method for treating a sumatriptan responsive state in a human, comprising iontophoretically administering to said human an amount of sumatriptan using a current of 4.0 mA or greater for at least a portion of the treatment period, such that said sumatriptan responsive state in said human is treated,
   wherein the sumatriptan is administered such that an $AUC_{0-inf}$ of between about 67 and about 158 hr*ng/mL within a 95% confidence interval is achieved in the human's plasma; and
   wherein the sumatriptan is administered such that a $C_{max}$ of between about 14 and about 38 ng/mL within a 95% confidence interval is achieved in the human's plasma.

15. The method of claim 14, wherein said portion of said treatment period is about thirty minutes to about 90 minutes.

16. The method of claim 14, wherein said method further comprises a low current treatment period using a current of between about 1.5 to about 2.5 mA.

17. The method of claim 16, wherein said low current treatment period uses a current of about 2.0 mA.

18. The method of claim 16, wherein said low current treatment period is between about 2 hours and about 4 hours in length.

19. The method of claim 14, wherein an effective amount of sumatriptan is administered without substantially irritating said human's skin.

20. The method of claim 19, wherein said iontophoretic administration of sumatriptan causes little or no erythema.

21. The method of claim 19, wherein said iontophoretic administration of sumatriptan causes little or no punctuate lesions.

22. The method of claim 14, wherein said sumatriptan responsive state is a migraine.

* * * * *